United States Patent [19]

Floyd, Jr. et al.

[11] 4,190,597

[45] Feb. 26, 1980

[54] VARIOUS 15-DEOXY-16-HYDROXY-16-ETHYNYL AND 16-ETHYNYLSUBSTITUTED PROSTAGLANDINS

[75] Inventors: Middleton B. Floyd, Jr., Suffern, N.Y.; Martin J. Weiss, Oradell, N.J.; Charles V. Grudzinskas, Nyack, N.Y.; Sow-mei L. Chen, Park Ridge, N.J.

[73] Assignee: American Cyanamid Company, Stamford, Conn.

[21] Appl. No.: 857,849

[22] Filed: Dec. 5, 1977

Related U.S. Application Data

[63] Continuation-in-part of Ser. No. 706,343, Jul. 19, 1976, Pat. No. 4,061,670.

[51] Int. Cl.$^2$ ............................................. C07C 177/00
[52] U.S. Cl. ............................ 260/448.2 D; 560/121; 562/503
[58] Field of Search ................ 560/121; 562/503; 260/448.2 D

[56] References Cited

U.S. PATENT DOCUMENTS 3,965,193  6/1976  Collins et al. ................ 560/121

*Primary Examiner*—Robert Gerstl
*Attorney, Agent, or Firm*—Norton S. Johnson

[57] ABSTRACT

15-Deoxy-16-hydroxy-16-ethynyl and 16-ethynylsubstituted prostanoic acids and congeners thereof, useful as bronchodilators, hypotensive agents, and as agents for the control of excessive gastric secretion.

47 Claims, No Drawings

VARIOUS 15-DEOXY-16-HYDROXY-16-ETHYNYL AND 16-ETHYNYLSUBSTITUTED PROSTAGLANDINS

This application is a continuation-in-part of our application Ser. No. 706,343 filed July 19, 1976, and now U.S. Pat. No. 4,061,670.

BACKGROUND OF THE INVENTION (1) Field of The Invention

The present invention relates to 15-deoxy-16-hydroxy-16-ethynyl and 16-substituted ethynyl prostaglandins, as well as the pharmaceutically acceptable, non-toxic lower alkyl esters and salts thereof, and to the intermediates and processes for producing such compounds.

(2) Description of The Prior Art

Prostaglandins have classically been described as chemically related 20 carbon chain hydroxy fatty acids having the basic skeleton of prostanoic acid:

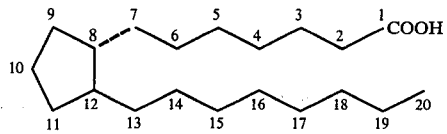

The prostaglandins having a hydroxyl group at the C-11 position and a keto group at the C-9 position are known as the PGE series, and those having a hydroxyl group in place of the keto group are known as the PGF series and are further designated by an α or β suffix to indicate the configuration of the hydroxyl group at said position. The natural compounds are the α-hydroxy substituted compounds. They may contain different degrees of unsaturation in the molecule, particularly at C-5, C-13 and C-17, the unsaturation is also indicated by a suffix. Thus, for example, the $PGF_1$ and $PGE_1$ series refer to prostanoic acids having a trans olefin bond at the C-13 position, while the $PGF_2$ and $PGE_2$ series refer to prostadienoic acids having a cis-olefin bond at the C-5 position and a trans olefin bond at the C-13 position. For a review on prostaglandins and the definition of primary prostaglandins, see, for example, S. Bergström, Recent Progress in Hormone Research 22, pp. 153–175 (1966) and Science 157, page 382 (1967) by the same author.

The preparation of derivatives of prostanoic acid has become of great importance since the demonstration of the highly interesting range of biological and pharmacological activities of natural prostaglandins.

The great majority of these studies have focused on modification of the two side chains, or modifications of the substituents attached to the cyclopentane moiety [see for example U. Axen et al, Synthesis Vol. 1, John Wiley and Sons Inc., New York, N.Y. 1973 and P. H. Bently, Chem. Soc. Reviews 2, 29 (1973)].

The synthesis of prostaglandin analogs possessing a 3-oxa- or 11-deoxy-3-thia moiety have been described, among others in U.S. Pat. No. 3,873,607; U.S. Pat. No. 3,950,406; Netherlands Pat. No. 7305222-Q; U.S. Pat. No. 3,944,593; U.S. Pat. No. 3,931,289; and U.S. Pat. No. 3,936,487.

The synthesis of several prostaglandin analogs wherein the hydroxyl group at C-15 has been removed and a hydroxyl group has been introduced at C-16 has appeared [see for example, U.S. Pat. No. 3,950,406; Prostaglandins, Vol. 10, 733 (1975); Tetrahedron Letters, No. 48, 4217 (1975)].

Recently reports have also appeared wherein the C-16 carbon bearing a hydroxyl group is substituted with a methyl group [see Pappo et al, Tetrahedron Letters, No. 4, 235 (1975); Collin et al, U.S. Pat. No. 3,965,143; and Belgium Patent No. 827,127].

SUMMARY OF THE INVENTION

In accordance with the present invention, we have prepared certain novel 15-deoxy-16-hydroxy-16-ethynyl and 16-substituted ethynyl-prostaglandin analogs represented by the following formula:

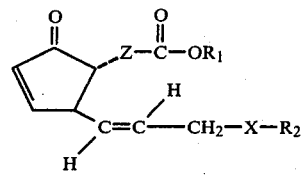

wherein $R_1$ is selected from the group consisting of hydrogen and $C_1$–$C_6$ alkyl; $R_2$ is selected from the group consisting of $C_3$–$C_7$ alkyl; X is selected from the group consisting of of a divalent moiety of the formulae:

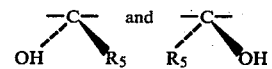

wherein $R_5$ is selected from the group consisting of ethynyl, 1-propynyl and trimethylsilylethynyl; Z is selected from the group consisting of a divalent moiety of the formulae. —(CH$_2$)$_4$-S-CH$_2$—,

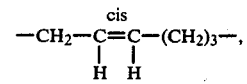

—(CH$_2$)$_6$— and —(CH$_2$)$_4$—O—CH$_2$; the racemic mixture thereof; and when $R_1$ is hydrogen, the pharmacological acceptable salts thereof.

The dotted lines shown in the above formula and in the formulas below indicate that the substituents are in α configuration, i.e., below the plane of the cyclopentane ring.

The double bond at C-13 in the compounds of the present invention has the same configuration as in natural prostaglandins of the PGE and PGF series, that is the trans configuration.

These novel compounds possess asymmetric centers and thus can be produced as racemic mixtures or as individual enantimers. The racemic mixtures can be resolved if desired at appropriate stages by methods known to those skilled in the art, to obtain the respective individual antimers. It is to be understood that the racemic mixtures and the individual 8R-antimers are encompassed within the scope of the present invention.

When the compounds of the present invention are racemic mixtures, they are produced starting from racemates, while when the compounds of the invention are individual antimers the compounds are preferably obtained starting from the appropriate individual antimer.

Useful pharmacologically acceptable salts of the above formula, where $R_1$ is hydrogen, are those with pharmacologically acceptable metal cations, ammonium, amine cations or quaternary ammonium cations.

Preferred metal cations are those derived from the alkali metals, e.g. lithium, sodium and potassium, and from the alkaline earth metals, e.g. magnesium and calcium, although cationic forms of other metals, e.g. aluminum, zinc and iron, are within the scope of this invention.

Pharmacologically acceptable amine cations are those derived from primary, secondary or tertiary amines such as mono-, di- or trimethylamine, ethylamine, dibutylamine, triisopropylamine, N-methylhexylamine, decylamine, dodecylamine, allylamine, crotylamine, cyclopentylamine, dicyclohexylamine, mono- or dibenzylamine, α- or β-phenylethylamine, ethylenediamine, diethylenetriamine, and aryliphatic amines containing up to and including 18 carbons atoms, as well as heterocyclic amines, e.g. piperidine, morpholine, pyrrolidine, piperazine and lower alkyl derivatives thereof, e.g. 1-methylpiperidine, 4-ethylmorpholine, 1-isopropylpyrrolidine, 2-methylpyrrolidine, 1,4-dimethylpiperazine, 2-methylpiperidine, and the like, as well as amines containing water-solubilizing or hydrophilic groups, e.g. mono-, di-, or triethanolamine, ethyldiethanolamine, N-butylethanolamine, 2-amino-1-butanol, 2-amino-2-ethyl-1,3-propanediol, 2-amino-2-methyl-1-propanol, tris(hydroxy-methyl)aminomethane, N-phenylethanolamine, N-(p-tert-amylphenyl)diethanolamine, galactamine, N-methylglucamine, N-methylglucosamine, ephedrine, phenylephrine, epinephrine, procaine, and the like.

Examples of suitable pharmacologically acceptable quaternary ammonium cations are tetramethylammonium, tetraethylammonium, benzyltrimethylammonium, phenyltriethylammonium and the like.

DISCLOSURE

The novel compounds of this invention can be prepared by a 1,4-conjugate-addition procedure involving treatment of the ether blocked cyclopentenone (18) with a lithio-cuprate reagent such as (8) or (14) prepared as illustrated in Flowsheets A, B, C and D.

FLOWSHEET A

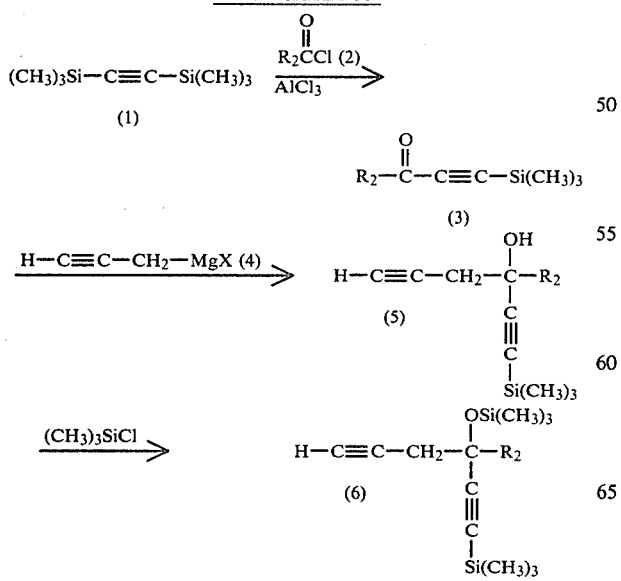

-continued

FLOWSHEET A

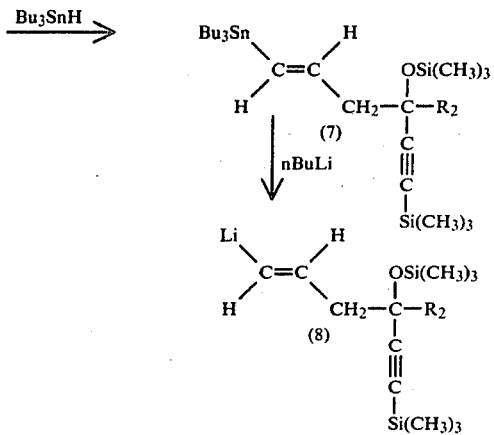

In accordance with the procedure outlined in Flowsheet A, treatment of bistrimethylsilylacetylene (1) with an acid chloride (2) in the presence of aluminum trichloride provides the acylacetylene (3). Treatment of acylacetylene (3) with proparglyic magnesium halide (4) forms the diacetylenic alcohol (5) which is silylated with chlorotrimethylsilane to provide the silyl ether (6). The silyl ether (6) is converted to the vinylstannane (7) by treatment with tributylstannane in the presence of azobisisobutrylnitrile.

FLOWSHEET B

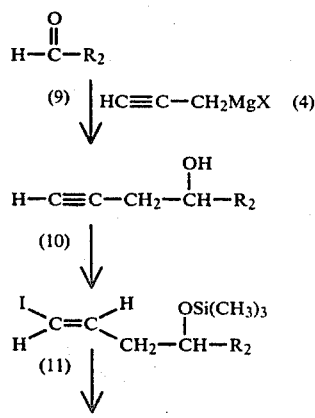

-continued
FLOWSHEET B

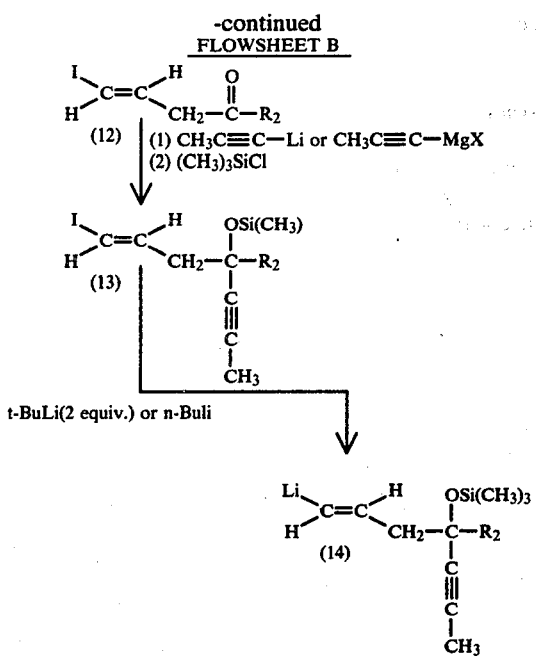

Treatment of the vinylstannyl reagent (7) with n-butyl lithium at a temperature of −10° C. to −78° C. generates the vinyl lithium reagent (8).

In accordance with the procedure as outlined in Flowsheet B, an aldehyde (9) is treated with propargylic magnesium halide (4) to form the homopropargylic alcohol (10), which is converted to its trimethylsilyl ether in the usual manner. The silylated derivative is then treated with disiamylborane (prepared in situ in tetrahydrofuran solution at ice bath temperature from 2-methyl-2-butene, sodium borohydride and boron trifluoride ethereate) and then anhydrous trimethylamine oxide. The resulting solution and an iodine solution in tetrahydrofuran are then added simultaneously to an aqueous solution of sodium hydroxide to give the 1-iodo-4-trimethylsilyloxy-trans-1-alkene (11).

The trimethylsilyl protecting group is removed with mild acid and the resulting vinyl iodide alcohol is oxidized with pyridinium chlorochromate to provide the 1-iodo-4-oxo-trans-1-alkene (12) which upon treatment with a Grignard reagent ($R_5MgX$) or alkyl lithium ($R_5Li$) provides the 1-iodo-4-hydroxy-trans-1-alkene, which is silylated in the usual manner to provide the silyl ether (13).

Treatment of (13) at low temperature, preferably −30° C. to −78° C. in an inert solvent, e.g. hexane, ether or toluene, with an alkyl lithium, e.g. n-butyl lithium or t-butyl lithium (2 equivalents) provides the trans-1-alkenyl lithium reagent (14). In the case of the vinylstannyl (7), n-butyl lithium is preferred for the generation of the vinyl lithium reagent.

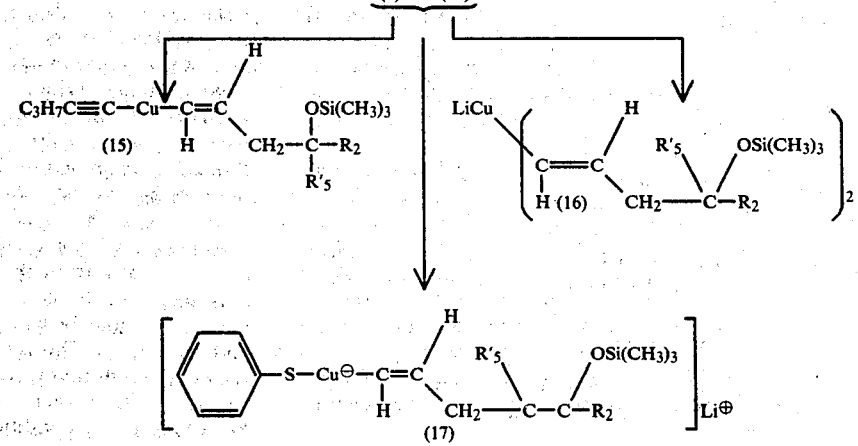

FLOWSHEET C

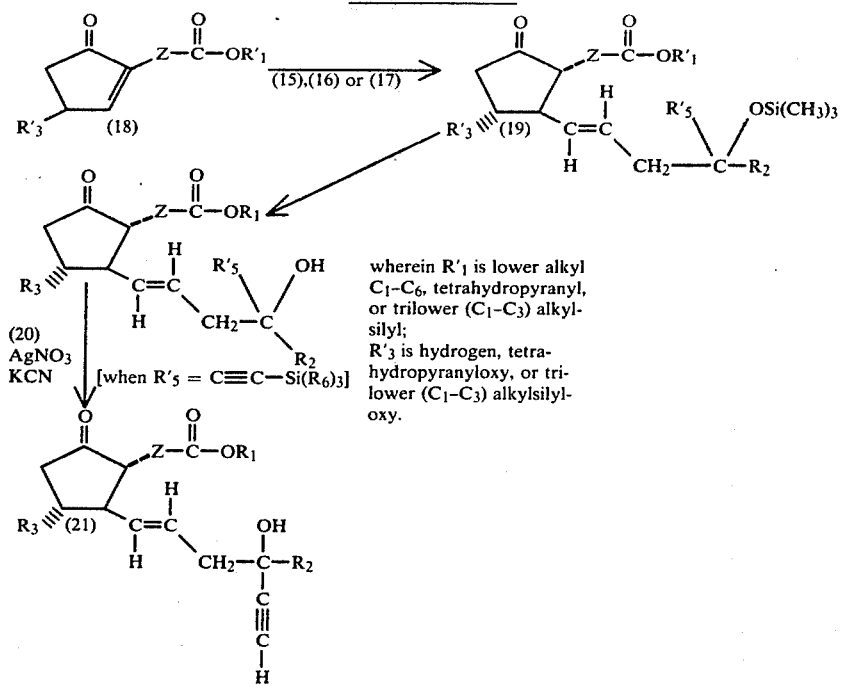

wherein R′₁ is lower alkyl C₁–C₆, tetrahydropyranyl, or trilower (C₁–C₃) alkylsilyl;
R′₃ is hydrogen, tetrahydropyranyloxy, or trilower (C₁–C₃) alkylsilyloxy.

In accordance with Flowsheet C, for the preparation of the asymmetrical lithio cuprate (15), wherein R′₅ is —C≡C—CH₃ or —C≡C—Si(R₆)₃, or the like, a solution of one molar equivalent of copper (I)-1-alkyne, preferably copper (I)-1-pentyne in anhydrous tributylphosphine or HMPTA, preferably one to five molar equivalents, in ether is added to one molar equivalent of the aforementioned vinyl lithium solution cooled to about −78° C. After about one hour at this temperature, a molar equivalent of the requisite cyclopentenone (18) is added. After several hours at −30° C. to −70° C. the reaction mixture is quenched with aqueous ammonium chloride solution and the blocked product (19) is isolated in the usual manner.

It is also possible to effect conjugate 1,4-addition with the asymmetrical lithio cuprate (17) wherein R′₅ is —C≡C—CH₃ or —C≡C—Si(R₆)₃ derived from vinyl lithium and cuprous thiophenoxide. A solution of vinyl lithium (8) or (14) in ether at −78° C. is reacted with an equimolar amount of a reagent prepared by admixture, in ether at a temperature of 0° C. to −78° C., of equimolar amounts of cuprous thiophenoxide and copper (I) iodide tributylphosphonium complex. After about 30 minutes at this temperature, the lithio cuprate (17) is treated with the requisite cyclopentenone (18) as described hereinabove for the conjugate addition with 1-alkynyl lithio cuprate (16).

For the preparation of the symmetrical lithio cuprate (16) wherein R′₅ is —C≡C—CH₃ or —C≡C—Si(R₆)₃ one molar equivalent of copper (I) iodide tributylphosphine complex, dissolved in anhydrous ether, is added at about −78° C. to two molar equivalents of the aforementioned vinyl lithium (8) or (14) solution cooled to −78° C. After about one hour at this temperature, the lithio cuprate (16) is treated with the requisite cyclopentenone (18) as described hereinabove for the conjugate addition with the 1-alkynyl lithio cuprate (15).

The procedures for conjugate addition involving organocopper reagents are well known in the art, see for example C. J. Sih, et al, J. Amer. Chem. Soc., 97, 865 (1975).

In the cases where R′₁=trimethylsilyloxy in cyclopentenone (18) the conjugate addition is performed at −78° C. to −40° C. The reaction is quenched by addition of an ether solution of acetic acid. Removal of blocking groups is then carried out as described in the reference above to provide the product (20) wherein R₁, R₂ are as hereinabove defined and R″₃ is hydrogen or hydroxyl.

To prepare the prostaglandin wherein the R₅ group at C-16 is —C≡C-H, the precursor (20) wherein R₅ is —C≡C—Si(R₆)₃ is treated with aqueous silver nitrate, to cleave the silylcarbon bond. An alternate procedure involves the use of silver salts such as AgBF₄.

The introduction of a racemic β-chain possessing the 16-hydroxy-16-ethynyl moieties provides a pair of prostaglandins epimeric at C-16. These two epimers may be separated into their upper (less polar) and lower (more polar) components by high-pressure liquid chromatography (HPLC) or by dry-column or preparative thin layer silica-gel chromatography.

All available evidence leads us to believe that the —CH≡CH— function introduced by the cuprate process occupies a position trans to the 11-oxy function. Similarly, we are led to the conclusion that in the product (19) the two side-chains attached to C₈ and C₁₂ are trans to each other. However, we are not certain of this configurational relationship in the product as it is obtained directly from the cuprate process. These products may have the side-chains in a trans- or cis-relationship or they may be a mixture containing both the trans- and cis-isomers. This is indicated in the nomenclature of the compounds involved by the designation 8ξ. In order to ensure a trans-relationship in (19) these products can be submitted to conditions known in the literature to equilibrate the cis-8-iso-PGE$_1$ to a mixture containing about 90% of the trans product. These conditions involve treatment with potassium acetate in aqueous methanol for 96 hours at room temperature.

The triloweralkylsilyloxy substituted lithio cuprate reagents of type (8) and (14) and their iodo and trialkylstannyl precursors are novel and useful compounds which are also embraced by this invention. They may be defined by generic formulae (B) and (C).

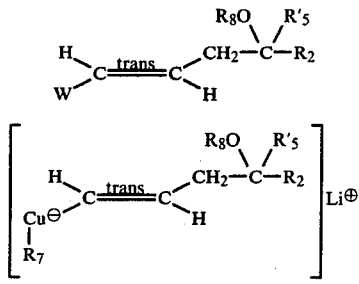

wherein W is iodine, tri n-butylstannyl or lithium, R$_2$ and R$'_5$ are as hereinabove defined, R$_8$ is triloweralkylsilyl, R$_7$ is thiopheneoxide, substituted thiopheneoxide, an alkyne or the identical vinyl moiety.

The cyclopentenones required for the preparation of the E$_1$, E$_2$, 3-oxa, and 11-deoxy-3-thia series have been discribed in the literature. The cyclopentenone for the preparation of 3-thia-11-hydroxy prostaglandins is described in Flowsheet D.

In accordance with Flowsheet D which is hereinbelow described, treatment of 2-furyl lithium (22A) with a ω-chloroaldehyde (22B) provides the chloroalcohol (22C). Treatment of the chloroalcohol (22C) with ethylmercaptoacetate furnishes the hydroxyester (22D) which upon hydrolysis with sodium formate/formic acid provides the 3-hydroxy-cyclopentenone (22E). Treatment of the cyclopentenone (22E) with sulfuric acid provides the required 4-hydroxy-cyclopentenone (22F) which after treatment with chlorotrimethylsilane provides the bissilylated cyclopentenone (22G).

FLOWSHEET D

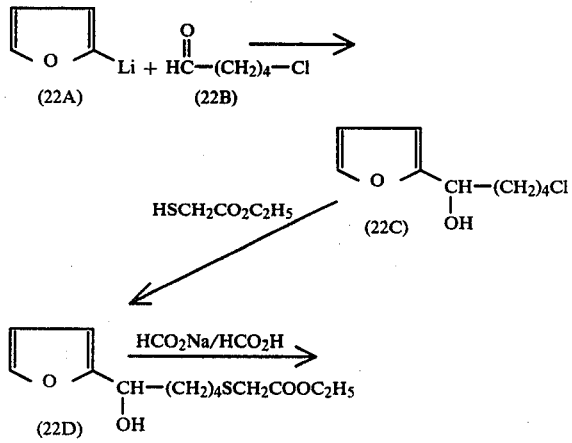

-continued
FLOWSHEET D

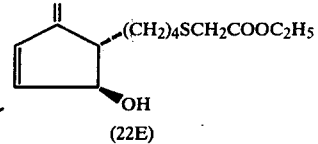

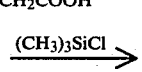
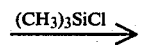

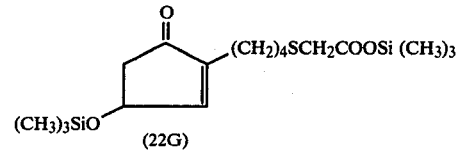

In accordance with Flowsheet E, when the 11-hydroxy or 11-oxy derivatives are treated with dilute acid, it is possible to effect elimination and the formation of the corresponding Δ$^{10}$ derivatives (22H) of the prostaglandin A-type. A preferred procedure involves treatment in tetrahydrofuran:water (2:1) solvent 0.5 N in HCl for about 30 hours at ambient temperature. Under these conditions a tetrahydropyranyl or trialkylsilyl ester or ether will undergo hydrolysis.

FLOWSHEET E

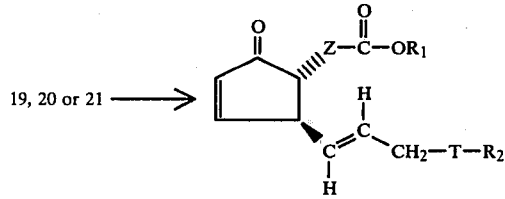

The prostaglandin carboxylic acids of this invention can be readily converted to the various alkyl esters of this invention by treatment in the usual manner with the appropriate diazoalkane. The preparation of diazoalkanes by various procedures are well described in the art. See for example C. D. Gutsche, Organic Reactions, VIII, 389 (1954). Certain of the esters of this invention can also be obtained directly by use of the appropriate cyclopentenone ester. The various esters can also be prepared by any of several procedures well-known in the art via an acid chloride (prior blocking of free alcohol groups with appropriate blocking groups such as trialkylsilyl, tetrahydropyranyl and the like) or mixed anhydrides and treatment of these intermediates with the appropriate alcohol. Mixed anhydrides can be obtained by treatment of the prostaglandin acid in a solvent such as dioxane at a temperature in the range of 0° C. to 15° C. with a molar equivalent of a tri-alkylamine, preferably triethylamine, tributylamine and the like, and then a molar equivalent of isobutyl chlorocarbonate or the like. The resulting mixed anhydrides are then treated with the appropriate alcohol to give the derivatized product. [For a pertinent literature analogy see Prostaglandins, 4, 768 (1973).]

An alternative procedure involves treatment of the prostaglandin acid with a molar equivalent of the trialkyl amine in an excess of the appropriate alcohol in an anhydrous solvent such as methylene chloride, a molar equivalent of p-toluenesulfonyl chloride is then added (if necessary, a second molar equivalent can be added) and after stirring at ambient temperatures for about 15 minutes to one hour the product is worked-up in the usual manner. (For a pertinent literature analogy, see U.S. Pat. No. 3,821,279.) A third procedure involves the use of dicyclohexylcarbodiimide in the usual manner; for a pertinent literature analogy see German Offen. 2,365,205; Chem. Abst., 81, 12009Bg (1974).

The esterified alcohol derivatives of this invention are also prepared in the usual manner by procedures well known in the art from the appropriate alkanoic acid anhydride or acid chloride.

When the compounds of this invention are prepared from racemic starting compounds, two racemates are obtained. In appropriate instances these racemates may be separated from each other by careful application of the usual chromatographic procedures. In the more difficult instances it may be necessary to apply high pressure liquid chromatography including recycling techniques. [See G. Fallick, American Laboratory, 19–27 (August 1973) as well as references cited therein. Additional information, concerning high speed liquid chromatography and the instruments necessary for its application, is available from Waters Associate Inc., Maple Street, Milford, Mass.]

In the following formulae Z is as hereinabove defined.

The 4-hydroxycyclopentenone racemates may be resolved into their component enantiomers (23) and (24) wherein Z is as hereinabove defined by derivatizing the ketone function with a reagent having an optically active center. The resulting diastereoisomeric mixture can then be separated by fractional crystallization, or by chromatography, or by high speed liquid chromatography involving, if necessary, recycling techniques. Among the useful optically active ketone derivatizing reagents are 1-α-aminoxy-α-methylpentanoic acid hydrochloride (to give 25), (R)-2-aminoxy-3,3-dimethylbutyric acid hydrochloride, and 4-α-methylbenzyl semicarbazide. After separation of the diastereomeric derivatives, reconstitution of the keto function provides the individual 4-hydroxycyclopentenone enantiomers (23) and (24). A useful procedure for the resoltuion of a 4-hydroxycyclopentenone racemate via an oxime such as (25) is described in the art [R. Pappo, P. Collins and C. Jung, Tetrahedron Letters, 943 (1973)]. The resolution of the hydroxycyclopentenone (23) wherein Z is

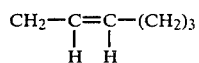

is described by Bruhn et al, Tetrahedron Letters, 235 (1976).

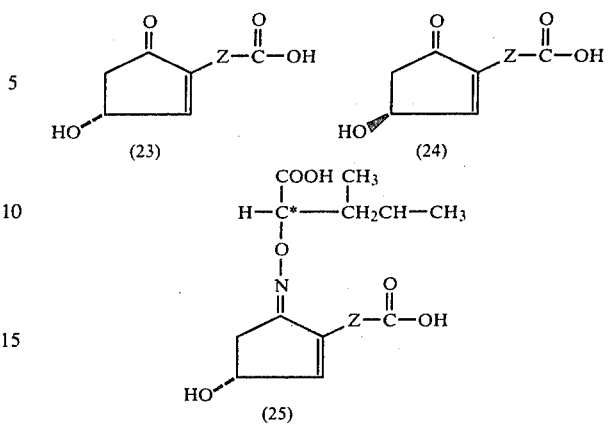

An alternative procedure for the preparation of the 4(R)-hydroxycyclopentenone enantiomers such as (23) involves as a key step the selective microbiological or chemical reduction of trione (26) to the 4(R)-hydroxycyclopentanedione (27). A wide variety of microorganisms are capable of accomplishing this asymmetric reduction, one of the most useful being *Dipodascus unincleatus*.

Conversion of hydroxycyclopentanedione (27) to an enol ether or enol ester, (28), (E=alkyl, preferably isopropyl; aroyl such as benzoyl; or arylsulfonyl such as 2-mesitylenesulfonyl), is accomplished by treatment, for example, with isopropyl iodide and a base such as potassium carbonate in refluxing acetone for from 15 to 20 hours, or with a base such as triethylamine and 0.95 equivalents of benzoyl chloride or a slight excess of 2-mesitylenesulfonyl chloride, in a non-prototropic solvent at a temperature of about −10° C. to −15° C. Reduction of (28) with excess sodium bis(2-methoxyethoxy)aluminum hydride in a solvent such as tetrahydrofuran or toluene at low temperatures, such as −60° C. to −78° C., followed by mild acid hydrolysis (representative conditions: aqueous dilute hydrochloric acid, pH 2.5; or oxalic acid, sodium oxalate in chloroform) at ambient temperatures from 1 to 3 hours provides the 4(R)-hydroxycyclopentenone ester (29). The ester (29) after blocking the hydroxy function as described hereinabove, can be subjected to conjugate addition reactions also as described hereinabove. The conjugate addition product, after deblocking the 11- and 15-hydroxy groups, will then be a methyl ester which can be hydrolyzed to the corresponding carboxylic acid by enzymatic or microbiological procedures, for example with baker's yeast or by exposure to *Rhizopus oryzae*.

For a description of these procedures in the art see: C. J. Sih, et al, J. A. C. S., 95, 1676 (1973); J. B. Heather, et al, *Tetrahedron Letters*, 2213 (1973); R. Pappo and P. W. Collins, *Tetrahedron Letters*, 2627 (1972); R. Pappo, P. Collins and C. Jung, Ann. N.Y. Acad. Sci., 180, 64 (1971); C. J. Sih, et al, J. A. C. S. 97, 865 (1975). For a description of the baker's yeast procedure see C. J. Sih, et al, J. A. C. S., 94, 3643 (1972).

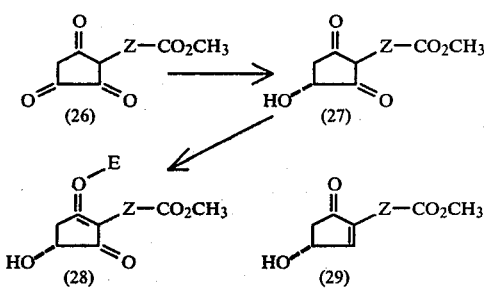

Procedures for the preparation of the requisite cyclopentanetriones (26) are well-established in the art and generally involve the treatment of an ω-1 oxo long chain ester (30) with methyl or ethyl oxalate and a base such as sodium methoxide in methanol, followed by treatment with dilute hydrochloric acid in aqueous methanol to effect the dealkoxyalylation of the intermediate (31). See J. Kutsube and M. Matsui, Agr. Biol. Chem., 33, 1078 (1969); P. Collins, C. J. Jung and R. Pappo, *Israel Journal of Chemistry*, 6, 839 (1968); R. Pappo, P. Collins and C. Jung, Ann. N.Y. Acad. Sci., 180, 64 (1971); C. J. Sih, et al, J. A. C. S., 95, 1676 (1973) (see reference 7); and J. B. Heather, et al, *Tetrahedron Letters*, 2313 (1973) for pertinent background literature.

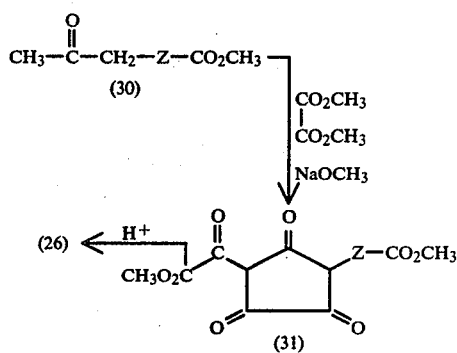

The intermediate keto esters (30) may be prepared by a variety of methods known to the art. One useful procedure is outlined below and involves alkylation of ethyl acetoacetate sodium salt (32) [in the usual manner with the appropriate side-chain precursor (33) X=Cl, Br, I, preferably Br or I] followed by decarbethoxylation and reesterification, all in the usual manner.

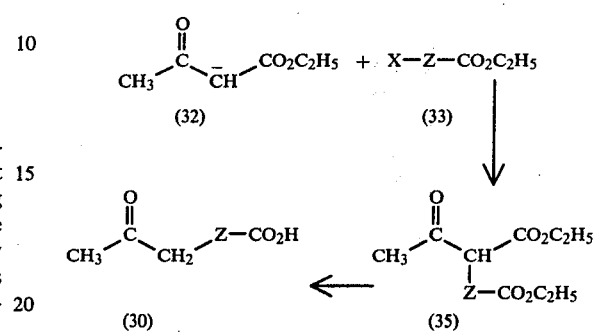

It is also possible to resolve the 4-hydroxycyclopentenone racemate (36) by microbiological means. Thus, treatment of the 4-O-alkanoyl or aroyl derivatives (37) ($R_{12}$=aryl or alkyl) of racemate (36) (preferably the 4-O-acetyl and 4-O-propionyl derivatives) with an appropriate microorganism, preferably a Saccharomyces species, e.g. 1375-143, affords preferential de-O-acylation of the 4(R)-enantiomer to give (23), which is then separated from the unreacted 4-(S)-O-acyl enantiomer (38) by chromatographic procedures. After separation, mild hydrolysis of the 4(S) derivative (38) provides the 4(S)-hydroxycyclopentenone (24) [See N. J. Marscheck and M. Miyano, Biochimica et Biophysica Acta, 316, 363 (1973) for related examples.]

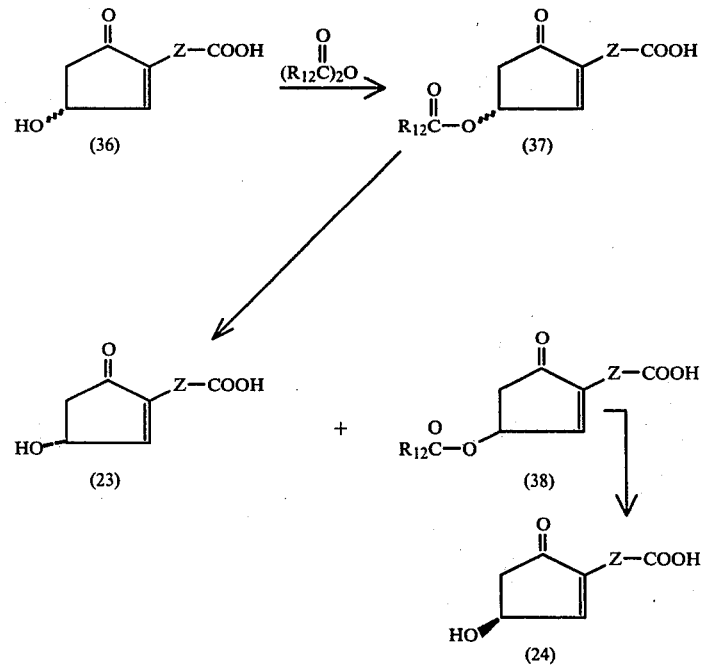

It is also possible to prepare the individual 4-hydroxycyclopentenones (23) and (24) directly by selective microbial hydroxylations of the corresponding 4-unsubstituted cyclopentenone (39). For example, with *Aspergillus niger* ATCC 9142; a selective 4(R)-hydroxylation of (39) [Z=(CH$_2$)$_6$] has been reported; for a literature example, see S. Kurozumi, T. Tora and S. Ishimoto, *Tetrahedron Letters*, 4959 (1973). Other organisms can also accomplish this hydroxylation.

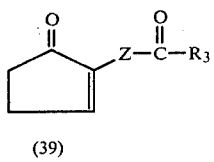

(39)

An alternate resolution procedure involves derivatization of the alcohol function of the racemic hydroxycyclopentenone to give ester-acid derivatives such as (40) wherein R"$_3$ is hydrogen or an alkyl group, n' is zero or two and Z is as hereinabove defined.

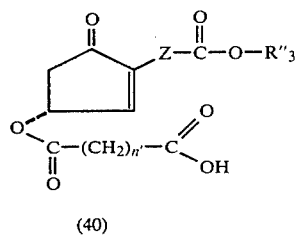

(40)

Such derivatives may be obtained from the corresponding free hydroxycyclopentenone by treatment in the usual manner with oxalyl chloride, succinyl chloride, succinic anhydride and the like. Treatment of the resulting acid or diacid (R"$_3$=hydrogen) with optically active amines e.g., 1-(−)-α-methylbenzylamine, d-(+)-α-methylbenzylamine, brucine, dehydroabietylamine, strychnine, quinine, cinchonine, quinidine, ephedrine, (+)-α-amino-1-butanol and the like, and fractional recrystallization of the resulting diastereomeric mixtures, followed by cleavage of the 4-oxy ester function in each of the individually isolated diastereomers provides the individual 4(S)- and 4(R)-hydroxycyclopentenone enantiomers (23) and (24) or their respective esters. Cleavage of the oxalate acid ester (40 n=O) can be accomplished by treatment with lead tetraacetate in pyridine solution. For an example of a similar use of oxalate acid-esters see J. G. Molotkovsky and L. D. Bergelson, *Tetrahedron Letters*, 4791 (No. 50, 1971); for an example of the use of succinate acid-ester see B. Goffinet, Ger. Offen. 2,263,880; Chem. Abstracts, 79, 78215$_z$ (1973).

Additional procedures, well-understood in the literature, for effecting the resolution of racemic prostenoic acids and esters of this invention are described below.

In these procedures a 9-oxo-11α,16(S)-16-substituted-dihydroxy-5-cis, 13-trans-prostadienoic acid and its 9α-hydroxy derivative are used for illustrative purposes, it being understood, however, that the procedures are general and have applicability to the other products of this invention, particularly to those derivatives wherein the 11-position is not substituted with an oxy function.

Conversion of a 9α-hydroxy racemate [the component enantiomers are illustrated by (41) and (42) below] wherein the C$_{11}$ and C$_{16}$ hydroxy functions are preferentially blocked as tetrahydropyranyl or trialkylsilyl ethers and conversion of the diacid (e.g., 41) to a bis salt (e.g., 43) with an optically active amine (e.g., 1-(−)-α-methylbenzylamine, d-(+)-α-methylbenzylamine, brucine, dehydroabietylamine, strychnine, quinine, cinchonine, cinchonindine, quinidine, ephedrine, deoxy ephedrine, amphetamine, (+)-2-amino-1-butanol, (−)-2-amino-1-butanol and the like). The resulting diastereomers could then be separated by fractional crystallization and the individual coomponents then converted by acidification and saponification to the individual optically active parent 9α-hydroxy enantiomers (41) and (42) oxidation of which after preferential blocking of the C$_{11}$ and C$_{16}$ hydroxy functions with tetrahydropyranyl or trialkylsilyl groups, provides the corresponding individual 9-oxo enantiomers (45) and (46) (for an appropriate literature procedure see E. W. Yankee, C. H. Lin and J. Fried, Journ. Chem. Soc., 1972, 1120).

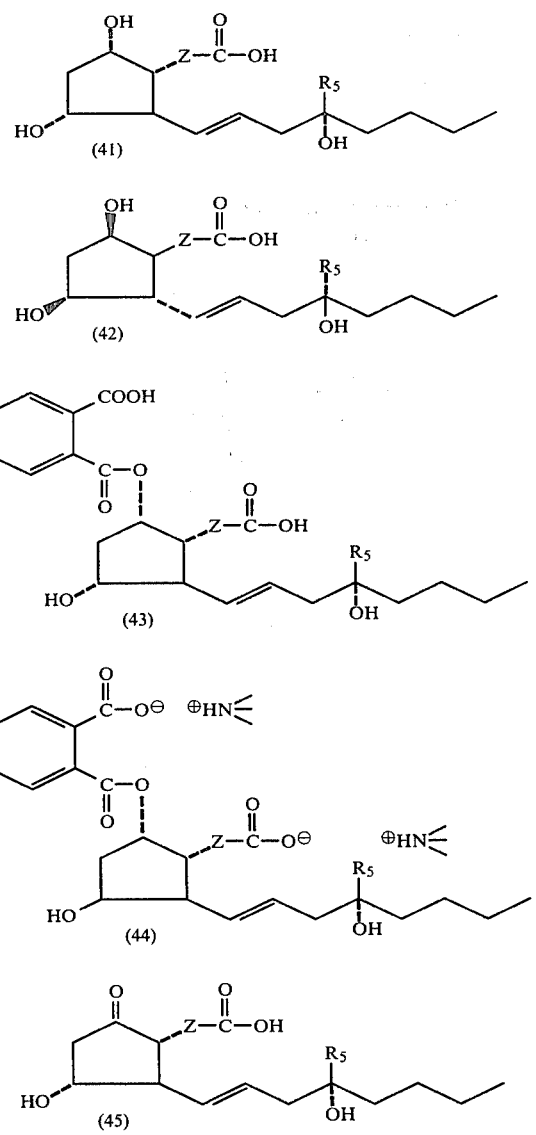

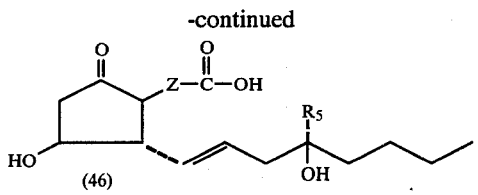

Another procedure involves conversion of the 9α-hydroxy racemate (as the prostenoic acid ester and with the $C_{11}$ and $C_{16}$ alcohol functions preferentially blocked as tetrahydropyranyl or trialkylsilyl ethers) to the diastereomeric carbamates with an optically active isocyanate, e.g., (+)-1-phenylethylisocyanate or (−)-1-phenylethylisocyanate, followed by deblocking. Separation of the diastereomers, for example (47) and (48) can be accomplished by fractional crystallization or by the usual chromatographic procedures, or if necessary by high speed liquid chromatography involving, if necessary, recycling techniques. Base-treatment of the individual diastereomeric carbamates affords the individual diastereomeric alcohols, for example (41) and (42).

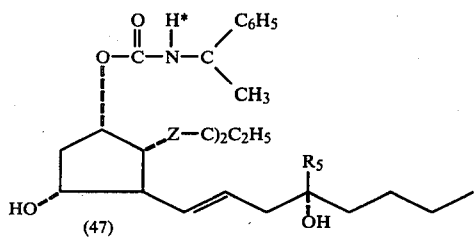

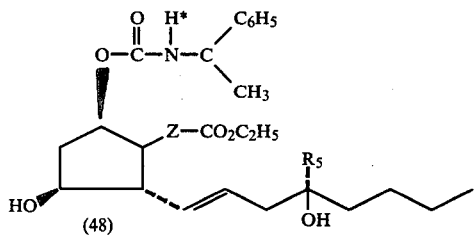

It is also possible to effect resolution of a 9α-hydroxy racemate, preferably as the prostenoate esters, by esterification of the 9α-hydroxy function (prior preferential blocking of $C_{11}$ and $C_{16}$ hydroxy functions as tetrahydropyranyl or trialkylsilyl ethers) with an optically active acid, via its acid chloride followed by deblocking the $C_{11}$ and $C_{16}$ alcohol groups. Suitable optically active acids include ω-camphoric acid, methoxyacetic acid, 3α-acetoxy-Δ$^5$-etianic acid, (−)-α-methoxy-α-trifluoromethylphenylacetic acid and (+)-α-methoxy-α-trifluoromethylphenylacetic acid and the like. The resulting diastereomeric esters, are then separated by fractional crystallization or by chromatographic techniques including, if necessary, the use of high speed liquid chromatography. Saponification of the individual diastereomers then provides the individual 9α-hydroxyprostenoic acid enantiomers (49) and (50).

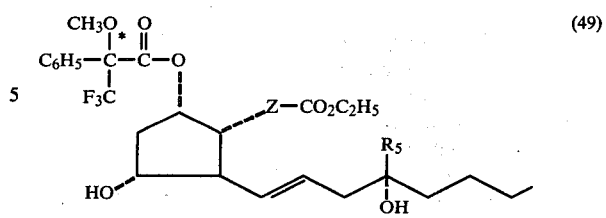

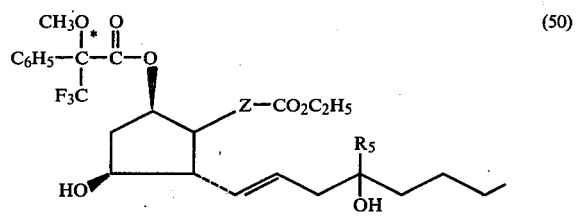

The novel compounds of the present invention have potential utility as hypotensive agents, anti-ulcer agents, agents for the treatment of gastric hypersecretion and gastric erosion, agents to provide protection against the ulcerogenic and other gastric difficulties associated with the use of various non-steroidal antiinflammatory agents (e.g. indomethacin, aspirin, and phenylbutazone), bronchodilators, anti-inflammatory agents, abortifacients, agents for the induction of labor, agents for the induction of menses, fertility-controlling agents, oestrus regulators for use in animal husbandry with cattle and other domestic animals and central nervous system regulatory agents. Certain of the novel compounds of this invention possess utility as intermediates for the preparation of other of the novel compounds of this invention.

The ring system of certain of the novel compounds of this invention allow them to be characterized as follows:

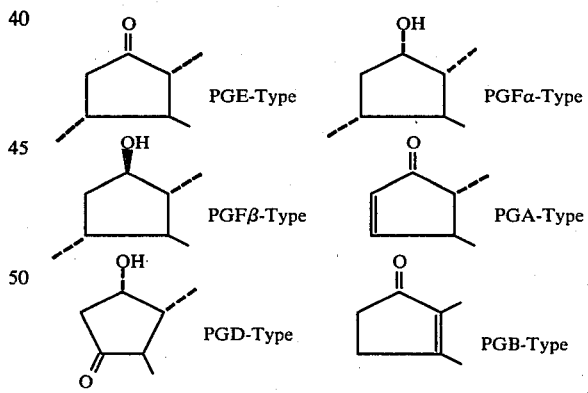

The known PGE compounds are all potent in causing multiple biological responses even at low doses. For example, $PGE_1$ and $PGE_2$ are extremely potent in causing vasodepression and smooth muscle stimulation, and also are potent as antilipolytic agents. Moreover, for many applications, these known prostaglandins have an inconveniently short duration of biological activity. In striking contrast, the novel prostaglandin analogs of this invention are substantially more specific with regard to potency in causing prostaglandin-like biological responses, and/or having a substantially, longer duration of biological activity. Therefore, each of these novel prostaglandin analogs is surprisingly and unexpectedly more useful than one of the corresponding above-mentioned known prostaglandins for at least one of the pharmacological purposes indicated below for the latter, either because it has a different and narrower spectrum of biological activity than the known prostaglandins, and therefore is more specific in its activity and causes smaller and fewer undesired side effects than the known prostaglandins, or because of its prolonged activity, fewer and smaller doses of the novel prostaglandin analog can frequently be used to attain the desired result.

Another advantage of the novel compounds of this invention, compared with the known prostaglandins, is that these novel compounds are administered effectively, orally, sublingually, intravaginally, buccally, or rectally, in addition to the usual intravenous, intramuscular or subcutaneous injection or infusion methods indicated above for the uses of the known prostaglandins. These qualities are advantageous because they facilitate maintaining uniform levles of these compounds in the body with fewer, shorter, or smaller doses, and make possible self-administration by the patient.

PGA compounds, and their esters and pharmacologically acceptable salts, are extremely potent in causing various biological responses. For that reason, these compounds are useful for pharmacological purposes. See, for example, Bergstron, et al., Pharmacol. Rev. 20, 1 (1968), and references cited therein. A few of those biological responses are systemic arterial blood pressure lowering in the case of the PGE compounds as measured, for example, in anesthetized (phenobarbital sodium) pentolinium-treated rats with indwelling aortic and right heart cannulas; stimulation of smooth muscle as shown, for example by tests on strips of guinea pig ileum, rabbit duodenum, or gerbil colon; potentiation of other smooth muscle stimulants; antilipolytic activity as shown by antagonism of epinephrine-induced mobilization of free fatty acids or inhibition of the spontaneous release of glycerol from isolated rat fat pads; inhibition of gastric secretion in the case of the PGA compounds as shown in dogs with secretion stimulated by food or histamine infusion; activity on the central nervous system.

Because of these biological responses, these known prostaglandins are useful to study, prevent, control, or alleviate a wide variety of disease and undesirable physiological conditions in birds and mammals, including humans, useful domestic animals, pets, and zoological specimens, and in laboratory animals, for example, mice, rats, rabbits, and monkeys.

For example, these compounds, are useful in mammals, including man, as nasal decongestants. For this purpose, the compounds are used in a dose range of about 10 $\mu$g per ml of a pharmacologically suitable liquid vehicle or as an aerosol spray, both for topical application.

The PGA compounds are useful in mammals, including man and certain useful animals, e.g., dogs and pigs, to reduce and control excessive gastric secretion, thereby reducing or avoiding gastric erosion or gastrointestinal ulcer formation, and accelerating the healing of such ulcers already present in the gastrointestinal tract. For this purpose, the compounds are injected or infused intravenously, subcutaneously, or intramuscularly in an infusion dose range of about 0.1 $\mu$g per kg of body weight per minute, or in a total daily dose by injection or infusion in the range of about 0.1 mg to about 20 mg per kg of body weight per day, the exact dose depending on the age, weight, and condition of the patient or animal, and on the frequency and route of administration. These compounds may also be useful in conjunction with various non-steroidal anti-inflammatroy agents, such as aspirin, phenylbutazone, indomethacin and the like, to minimize the well-known ulcerogenic effects of the latter.

The compounds are useful as hypotensive agents to reduce blood pressure in mammals including man. For this purpose, the compounds are administered by intravenous infusion at the rate of about 0.01 $\mu$g to about 50 $\Xi$g per kg of body weight per minute, or in a single or multiple doses of about 25 $\mu$g to 2500 $\mu$g per kg of body weight total per day.

The PGA compounds and derivatives and salts thereof increase the flow of blood in the mammalian kidney, thereby increasing volume and electrolyte content of the urine. For that reason, PGA compounds are useful in managing cases of renal disfunction, especially in cases of severe impaired renal blood flow, for example, the hepatorena syndrom and early kidney transplant rejection. In case of excessive or inappropriate ADH antidiuretic hormone vasopressin secretion, the diuretic effect of these compounds is even greater. In anephretic states, the vasopressin action of these compounds is especially useful. For that reason, these compounds are useful to promote and accelerate healing of skin which has been damaged, for example, by burns, wounds, and abrasions, and after surgery. These compounds are also useful to promote and accelerate adherence and growth of skin autografts, especially small, deep (Davis) grafts which are intended to cover skinless areas by subsequent outward growth rather than initially, and to retard rejection of homografts.

For these pruposes, these compounds are preferably administered topically at or near the site where cell growth and keratin formation is desired, advantageously as an aerosol liquid or micronized powder spray, as an isotonic aqueous solution in the case of wet dressings, or as a lotion, cream, or ointment in combination with the usual pharmaceutically acceptable diluents. In some instances, for example, when there is substantial fluid loss as in the case of extensive burns or skin loss due to other causes, systemic administration is advantageous, for example, by intravenous injection or infusion, separate or in combination with the usual infusions of blood, plasma, or substituents thereof. Alternative routes of administration are subcutaneous or intramuscular near the site, oral, sublingual, buccal, rectal, or vaginal. The exact dose depends on such factors as the route of administration, and the age, weight, and condition of the subject. To illustrate, a wet dressing for topical application to second and/or third degree burns of skin area 5 to 25 square centimeters would advantageously involve use of an isotonic aqueous solution containing 2 to 2000 $\mu$g/ml of the PGE compound. Especially for topical use, these prostaglandins are useful in combination with antibiotics, for example, gentamycin, neomycin, polymyxin B, bacitracin, spectinomycin and oxytetracycline, with other antibacterials, for example, mafenide hydrochloride, sulfadiazine, furazolium chloride, and nitrofurazone, and with corticoid steroids, for example, hydrocortisone, prednisolone, methylprednisolone, and fluoroprednisoline, each of those being used in combination at the usual concentrations suitable for its use alone.

The novel compounds of this invention induce the biological responses described hereinabove as associated with its particular prostaglandin type. These novel compounds are accordingly used for the above-described corresponding purposes.

The novel PGA compounds of this invention are also useful as bronchodilators for the treatment of asthma and chronic bronchitis. As such they may be conveniently administered by inhalation of aerosol sprays prepared in a dose range of about 10 μg to about 10 mg/ml of a pharmacologically suitable liquid vehicle. Relative to the natural prostaglandins, the PGE compounds in particular have the significant advantage of inducing prolonged effects.

DETAILED DISCLOSURE

The invention will be described in greater detail in conjunction with the following specific examples.

EXAMPLE 1 n-Butyl trimethylsilylethynyl ketone

To a stirred solution of 14.4 g of valeryl chloride and 20.4 g of bis-trimethylsilylacetylene in 300 ml of dry methylene chloride, cooled in an ice bath, is added powdered anhydrous aluminum chloride, portionwise, over a period of 20 minutes. The mixture is stirred for 5 minutes, then the cooling bath is removed and the mixture is stirred at room temperature for 4 hours. The mixture is poured into 500 ml of ice-water. The organic layer is separated, washed with water and brine, dried over anhydrous sodium sulfate and filtered through diatomaceous earth. The mother liquor is evaporated to dryness giving a brownish residue. This residue is Kugelrohr-distilled to give 16.56 g of colorless liquid at 45° C./0.3 mm which is essentially identical with the authentic product.

EXAMPLE 2

4-Trimethylsilylethynyl-1-octyn-4-ol

To a stirred suspension of 1.29 g of magnesium and 10 mg of mercuric chloride in 12 ml of ether is added 0.4 ml of propargyl bromide. The reaction is initiated after stirring at room temperature for a few minutes. The stirred mixture is cooled in an ice-water bath and a solution of 9.64 g of n-butyl trimethylsilylethynyl ketone and 3.51 ml of propargyl bromide in 13 ml of ether is added dropwise so that the mixture is very gently boiling during 40 minutes. After addition, the cooling bath is removed and the mixture is stirred at room temperature for 1.5 hours. The mixture is recooled in an ice bath and 10 ml of saturated ammonium chloride solution is added. The resulting white mixture is filtered through diatomaceous earth. The clear mother liquor is washed with saturated sodium chloride solution and dried over anhydrous magnesium sulfate. The solvent is evaporated to dryness giving 10.5 g of a red liquid. This liquid is Kugelrohr-distilled at 60° C./0.25–0.3 mm. The pale yellow liquid distillate which is the desired product weighs 8.5 g.

EXAMPLE 3

4-Trimethylsilylethynyl-1-octyn-4-ol trimethylsilyl ether

To a stirred mixture of 8.5 g of 4-trimethylsilylethynyl-1-octyn-4-ol and 6.2 g of imidazole in 24 ml of dry dimethylformamide is added, under nitrogen, 5.7 ml of chlorotrimethylsilane, in a slow stream, via a syringe. The mixture is stirred in an ice bath for one hour and then at room temperature overnight. The mixture is poured into hexane, washed with saturated sodium bicarbonate solution, water and then brine and dried over sodium sulfate. The solvents are evaporated to dryness giving 11.1 g of the desired product.

EXAMPLE 4

4-Trimethylsilylethynyl-4-trimethylsiloxy-1-octen-1-tri-n-butyl stannane

To a mixture of 10 mg of azobisisobutyronitrile and 2.94 g of 4-trimethylsilylethynyl-1-octyn-4-ol trimethylsilyl ether is added 2.65 ml of tri-n-butyl stannane via a syringe. The mixture is stirred and heated under nitrogen in an oil bath at 130° C. for 3 hours and then cooled to room temperature. This mixture is vacuum-distilled through a short-path distillation apparatus to remove a forerun at 40° C./0.4 mm. The yellow oil (pot residue) comprises the desired product.

EXAMPLE 5

15-Deoxy-16-hydroxy-16-trimethylsilylethynyl-PGE$_2$

A solution of 3.7 g of 4-trimethylsilylethynyl-4-trimethylsiloxy-1-octen-1-tri-n-butyl stannane in 3 ml of tetrahydrofuran is cooled in a dry ice-acetone bath under nitrogen, treated with 6.4 mmol of n-butyl lithium during 10 minutes, stirred at −70° C. for 5 minutes, then at −40° C. for one hour and finally at −40° C. to −30° C. for 30 minutes. Aliquots are quenched with water and assayed by NMR until the lithium exchange is shown to be complete after 1.5 hours at −40° C. to −30° C.

A second mixture of 830 mg of copper pentyne, 2.55 g of tri-n-butyl phosphene and 6 ml of ether is stirred at room temperature under nitrogen for about 20 minutes until a clear solution is obtained. This copper pentyne solution is transferred to the vinyl lithium solution (which is first recooled to −75° C. in a dry ice-acetone bath) via a syringe. After stirring at −75° C. for 2 hours, a solution of 2.1 g of cyclopentenone-bis-TMS [U.S. 3,873,607 (Example 1125)] is added during 10 minutes. The mixture is stirred at −78° C. for 10 minutes, then at −50° C. to −40° C. for one hour, then at −40° C. to −30° C. for 30 minutes and is then recooled to −50° C. The mixture is quenched by pouring it into a mixture of 200 ml of saturated ice-cold ammonium chloride solution and 100 ml of ether. The mixture is extracted with ethyl acetate. The combined ether-ethyl acetate extract is washed with water and brine. The solvents are evaporated to dryness. The residue is treated with 30 ml of acetic acid, 15 ml of tetrahydrofuran and 7.5 ml of water and stirred at room temperature under nitrogen for 30 minutes. A 50 ml portion of toluene is added and the mixture is evaporated to dryness. The residue is applied to 12 g of silica gel and then washed with 75 ml of hexane. The silica gel cake is washed with 150 ml of ethyl acetate. The ethyl acetate extract is passed through a dry 2 inch × 50 inch column of 610 g of silica gel and eluted with 450 ml of 70% ethyl acetate:1% acetic acid in hexane. The product is then eluted from the silica gel with ethyl acetate. The solvent is evaporated to dryness in the presence of toluene giving a total of 860 mg of the desired product.

EXAMPLE 6

15-Deoxy-16-hydroxy-16-ethynyl-PGE$_2$

To a solution of 300 mg of 15-deoxy-16-hydroxy-16-trimethylsilylethynyl-PGE$_2$ in 1.2 ml of methanol is added dropwise a solution of 2.7 g of silver nitrate in 6 ml of water and 18 ml of ethanol. The mixture is then stirred at room temperature under nitrogen for one hour. One ml of a solution of one gram of potassium cyanate in 1.5 ml of water is added and the mixture is stirred at room temperature for 40 minutes. Water is added to dissolve the resulting white precipitate and the solution is neutralized with 5% hydrochloric acid. The white solid which forms is removed. The mother liquor is extracted with ether-ethyl acetate and the organic phase is washed with water and brine, filtered and evaporated to dryness. The residue is purified through a 200 g silica gel column (1 3/16 inch×45 inch) eluting with 70% ethyl acetate:1% acetic acid in hexane. The product fraction is eluted from the column with ethyl acetate. The solvent is evaporated to dryness in the presence of toluene giving 240 mg of the desired product as an oily residue.

EXAMPLES 7-8

Treatment of the acid chlorides of Table 1 by the procedure of Example 1 with bis-trimethylsilylacetylene is productive of the ketones of Table 1.

TABLE 1

| Example | Starting Acid Chloride | Product Alkyl Trimethyl-silylethynyl Ketone |
|---|---|---|
| 7 | butyryl chloride | n-propyl trimethylsilyl-ethynyl ketone |
| 8 | heptanoyl chloride | n-hexyl trimethylsilyl-ethynyl ketone |

EXAMPLES 9-10

Treatment of the ketones of Table 2 by the procedure of Example 3 is productive of the 4-trimethylsilylethynyl-1-alkyn-4-ol's of the Table.

TABLE 2

| Example | Starting Ketone | Product 4-Trimethylsilyl-ethynyl-1-alkyn-4-ol |
|---|---|---|
| 9 | 7 | 4-trimethylsilylethynyl-1-heptyn-4-ol |
| 10 | 8 | 4-trimethylsilylethynyl-1-decyn-4-ol |

EXAMPLES 11-12

Treatment of the alkyn-4-ol's of Table 3 with chlorotrimethylsilane by the procedure of Example 3 followed by treatment of the resulting trimethylsilylether with tri-n-butylstannane by the procedure of Example 4 is productive of alkenes of the Table.

TABLE 3

| Example | Starting Alkyn-4-ol | Product Alkene |
|---|---|---|
| 11 | 9 | (E)4-trimethylsilylethynyl-4-trimethylsiloxy-1-tri-n-butylstannane-1-heptene |
| 12 | 10 | (E)4-trimethylethynyl-4-trimethylsilyloxy-1-tri-n-butylstannane-1-decene |

EXAMPLE 13

Preparation of 4-Trimethylsiloxy-1-octyne

To a cold solution of 166 g of 4-hydroxy-1-octyne [Prostaglandins, 10, 289 (1975)], and 240 g of imidazole in one liter of dimethylformamide is added dropwise 202 g of chlorotrimethylsilane. The mixture is allowed to stand at room temperature for 2 to 3 days. The mixture is partitioned with water and hexane. The hexane layer is washed with brine, dried over magnesium sulfate, and concentrated. Distillation of the residue gives a colorless liquid, b.p. 38° (0.2 mm).

EXAMPLE 14

Preparation of 1-Iodo-4-trimethylsiloxy-trans-1-octene

To a stirred solution of 0.20 moles of freshly prepared bis-(3-methyl-2-butyl)borane in 300 ml of tetrahydrofuran at 0°-5° C. is added dropwise a solution of 19.8 g of 4-trimethylsiloxy-1-octyne in 30 ml of tetrahydrofuran. The resulting mixture is stirred at ambient temperature for several hours, cooled in an ice bath, and treated with 53 g of trimethylamine oxide. The mixture is stirred several hours at 25°-40° C. and then poured into 2 liters of 15% sodium hydroxide. The resulting mixture is treated immediately with a solution of 140 g of iodine in 300 ml of tetrahydrofuran. After 0.5 hour the organic phase is separated and the aqueous phase is extracted with ether. The combined organic layers are washed with water, sodium thiosulfate solution, and brine; dried over magnesium sulfate; and concentrated to give an oil, pmr spectrum (CDCl$_3$): 6.2 (d, ICH=) and 6.7 (quintuplet, =CH—).

EXAMPLE 15

Preparation of 4-Hydroxy-1-iodo-trans-1-octene

A 23 g portion of 1-iodo-4-trimethylsiloxy-trans-1-octene is dissolved in a mixture of 200 ml of glacial acetic acid, 100 ml of tetrahydrofuran, and 50 ml of water. After solution occurs, toluene is added and the mixture is evaporated. The resulting oil is chromatographed on silica gel with hexane progressively enriched in benzene followed by acetone to give 16 g of an oil, pmr spectrum (CDCl$_3$): 3.69 (m, CHOH) and 2.3 (s, OH).

EXAMPLE 16

Preparation of 4-Oxo-1-iodo-trans-1-octene

To a stirred suspension of 6.15 g of pyridinium chlorochromate (Tetrahedron Letters, 1975, 2647) in 20 ml of methylene chloride is added 450 mg of sodium acetate. After 5 minutes, a solution of 3.64 g of 4-hydroxy-1-iodo-trans-1-octene in 15 ml of methylene chloride is added in one portion. The dark mixture is stirred at room temperature for 75 minutes, diluted with 50 ml of ether, and decanted. The solid sludge is washed repeatedly with ether and decanted. The combined solutions are percolated through Florisil. The solution is concentrated to give and orange liquid, pmr spectrum (CDCl$_3$): 3.20 (d, j=7 cps, =CHCH$_2$CO).

EXAMPLE 17

Preparation of 4-Hydroxy-4-(1-propynyl)-1-iodo-trans-1-octene

To a stirred solution of propynyllithium at −25° is added a solution of 4-oxo-1-iodo-trans-1-octene in tetrahydrofuran. After the addition, the solution is stirred at −20° to −15° C. for 30 minutes. The reaction is quenched with a mixture of hexane and ice. The aqueous phase is separated and extracted with additional hexane. The combined hexane extracts are washed successively with water and brine. The solution is dried over magnesium sulfate and concentrated. The residue is subjected to column chromatography on silica gel with toluene to provide the product as an oil.

EXAMPLE 18

Preparation of 4-Hydroxy-4-(1-propenyl)-1-iodo-trans-1decene

Treatment of 4-hydroxy-1-decyne (U.S. Pat. 3,950,406) by the procedures of Examples 13, 14, 15, 16 and 17 is productive of the iodo-decene compound.

EXAMPLES 19–20

Treatment of the iodoalkenes of Table 4 with chlorotrimethylsilane by the procedure of Example 3 is productive of the trimethylsilylether of the Table.

TABLE 4

| Example | Starting iodo Alkene | Product Silylether |
|---|---|---|
| 19 | 17 | 4-trimethylsilyloxy-4-1-propoynyl)-1-iodo-trans-1-octene |
| 20 | 18 | 4-trimethylsilyloxy-4-(1-propoynyl)-1-iodo-trans-1-decene |

EXAMPLES 21–60

Treatment of the vinylstannyl or iodoalkene derivatives of Example 4, Table 3 and Table 4 with n-butyllithium by the procedure of Example 5, followed by cuprate formation according to Example 5, followed by treatment of the cuprate with the cyclopentenone of the Table according to the procedure of Example 5, is productive of the prostanoids of the Table.

TABLE 5

| Example | Starting Cyclopentenone | Product Prostanoid |
|---|---|---|
| 21 | 4-trimethylsilyloxy-2-(6-carbotrimethylsilyloxyhexyl)-cyclopent-2-en-1-one | 11α,16-dihydroxy-9-oxo-16-(trimethylsilylethynyl)-13-trans-prostenoic acid |
| 22 | 4-trimethylsilyloxy-2-(6-carbotrimethylsilyloxy-2-cis-hexenyl)-cyclopent-2-en-1-one | 11α,16-dihydroxy-9-oxo-16-(trimethylsilylethynyl)-5-cis,13-trans-prostadienoic acid |
| 23 | 4-trimethylsilyloxy-2-(6-carbotrimethylsilyloxy-5-thiahexyl)-cyclopent-2-en-1-one | 11α,16-dihydroxy-9-oxo-16-(trimethylsilylethynyl)-3-thia-13-trans-prostenoic acid |
| 24 | 4-trimethylsilyloxy-2-(6-carbotrimethylsilyloxy-5-oxahexyl)-cyclopent-2-en-1-one | 11α,16-dihydroxy-9-oxo-16-(trimethylsilylethynyl)-3-oxa-13-trans-prostenoic acid |
| 25 | 2-(6-carbethoxyhexyl)-cyclopent-2-en-1-one | methyl-16-hydroxy-9-oxo-16-(trimethylsilylethynyl)-13-trans-prostenoic acid |
| 26 | 2-(6-carbomethoxy-2-cis-hexenyl)-cyclopent-2-en-1-one | ethyl-16-hydroxy-9-oxo-16-(trimethylsilylethynyl)-5-cis,13-trans-prostenoic acid |
| 27 | 2-(6-carbethoxy-5-thiahexyl)-cyclopent-2-en-1-one | ethyl-16-hydroxy-9-oxo-16-(trimethylsilylethynyl)-3-thia-13-trans-prostenoate |
| 28 | 2-(6-carbethoxy-5-oxahexyl)-cyclopent-2-en-1-one | ethyl-16-hydroxy-9-oxo-16-(trimethylsilylethynyl)-3-oxa-13-trans-prostenoate |
| 29 | d-4-trimethylsilyloxy-2-(6-carbomethoxy-2-cis-hexenyl)-cyclopent-2-en-1-one | nat-methyl-11α,16-dihydroxy-9-oxo-16-(trimethylsilylethynyl)-5-cis,13-trans-prostadienoate |
| 30 | d-4-trimethylsilyloxy-2-(6-carbomethoxyhexyl)-cyclopent-2-en-1-one | nat-methyl-11α,16-dihydroxy-9-oxo-16-(trimethylsilylethynyl)-13-trans-prostenoate |
| 31 | 4-trimethylsilyloxy-2-(6-carbotrimethylsilyloxyhexyl)-cyclopent-2-en-1-one | 11α,16-dihydroxy-9-oxo-16-(1-propynyl)-13-trans-prostenoic acid |
| 32 | 4-trimethylsilyloxy-2-(6-carbotrimethylsilyloxy-2-cis-hexenyl)-cyclopent-2-en-1-one | 11α,16-dihydroxy-9-oxo-16-(1-propynyl)-5-cis,13-trans-prostadienoic acid |
| 33 | 4-trimethylsilyloxy-2-(6-carbotrimethylsilyloxy-5-thiahexyl)-cyclopent-2-en-1-one | 11α,16-dihydroxy-9-oxo-16-(1-propynyl)-3-thia-13-trans-prostenoic acid |
| 34 | 4-trimethylsilyloxy-2-(6-carbotrimethylsilyloxy-5-oxahexyl)-cyclopent-2-en-1-one | 11α,16-dihydroxy-9-oxo-16-(1-propynyl)-3-oxa-13-trans-prostenoic acid |
| 35 | 2-(6-carbethoxyhexyl)-cyclopent-2-en-1-one | methyl-16-hydroxy-9-oxo-16-(1-propynyl)-13-trans-prostenoate |
| 36 | 2-(6-carbomethoxy-2-cis-hexenyl)-cyclopent-2-en-1-one | ethyl-16-hydroxy-9-oxo-16-(1-propynyl)-5-cis,13-trans-prostadienoate |
| 37 | 2-(6-carbethoxy-5-thiahexyl)-cyclopent-2-en-1-one | ethyl-16-hydroxy-9-oxo-16-(1-propynyl)-3-thia-13-trans-prostenoate |
| 38 | 2-(6-carbethoxy-5-oxahexyl)-cyclopent-2-en-1-one | ethyl-16-hydroxy-9-oxo-16-(1-propynyl)-3-oxa-13-trans-prostenoate |
| 39 | d-4-trimethylsilyloxy-2-(6-carbomethoxy-2-cis-hexenyl)-cyclopent-2-en-1-one | nat-methyl-11α,16-dihydroxy-9-oxo-16-(1-propynyl)-5-cis,13-trans-prostadienoate |
| 40 | d-4-trimethylsilyloxy-2-(6-carbomethoxyhexyl)-cyclopent-2-en-1-one | nat-methyl-11α,16-dihydroxy-9-oxo-16-(1-propynyl)-13-trans-prostenoate |
| 41 | 4-trimethylsilyloxy-2-(6-carbotrimethylsilyloxyhexyl)-cyclopent-2-en-1-one | 11α,16-dihydroxy-9-oxo-16-(trimethylsilylethynyl)-20-ethyl-13-trans-prostenoic acid |
| 42 | 4-trimethylsilyloxy-2-(6-carbotrimethylsilyloxy-2-cis-hexenyl)-cyclopent-2-en-1-one | 11α,16-dihydroxy-9-oxo-16-(trimethylsilylethynyl)-20-ethyl-5-cis,13-trans-prostenoic acid |
| 43 | 4-trimethylsilyloxy-2-(6-carbotrimethylsilyloxy-5-thiahexyl)-cyclopent-2-en-1-one | 11α,16-dihydroxy-9-oxo-16-(trimethylsilylethynyl)-20-ethyl-3-thia-13-trans-prostenoic acid |
| 44 | 4-trimethylsilyloxy-2-(6-carbotrimethylsilyloxy-5-oxahexyl)-cyclopent-2-en-1-one | 11α,16-dihydroxy-9-oxo-16-(trimethylsilylethynyl)-20-ethyl-3-oxa-13-trans-prostenoic acid |
| 45 | 2-(6-carbethoxyhexyl)-cyclopent-2-en-1-one | methyl-16-hydroxy-9-oxo-16-(trimethylsilylethynyl)-20-ethyl-13-trans-prostenoate |

TABLE 5-continued

| Example | Starting Cyclopentenone | Product Prostanoid |
|---|---|---|
| 46 | 2-(6-carbomethoxy-2-cis-hexenyl)-cyclopent-2-en-1-one | ethyl-16-hydroxy-9-oxo-16-(trimethylsilylethynyl)-20-ethyl-5-cis,13-trans-prostadienoate |
| 47 | 2-(6-carbethoxy-5-thiahexyl)-cyclopent-2-en-1-one | ethyl-16-hydroxy-9-oxo-16-(trimethylsilylethynyl)-20-ethyl-3-thia-13-trans-prostenoate |
| 48 | 2-(6-carbethoxy-5-oxahexyl)-cyclopent-2-en-1-one | ethyl-16-hydroxy-9-oxo-16-(trimethylsilylethynyl)-20-ethyl-3-oxa-13-trans-prostenoate |
| 49 | d-4-trimethylsilyloxy-2-(6-carbomethoxy-2-cis-hexenyl)-cyclopent-2-en-1-one | nat-methyl-11α,16-dihydroxy-9-oxo-16-(trimethylsilylethynyl)-20-ethyl-5-cis,13-trans-prostadienoate |
| 50 | d-4-trimethylsilyloxy-2-(6-carbomethoxyhexyl)-cyclopent-2-en-1-one | nat-methyl-11α,16-dihydroxy-9-oxo-16-(trimethylsilylethynyl)-20-ethyl-13-trans-prostenoate |
| 51 | 4-trimethylsilyloxy-2-(6-carbotrimethylsilyloxyhexyl)-cyclopent-2-en-1-one | 11α,16-dihydroxy-9-oxo-16-(1-propynyl)-20-ethyl-13-trans-prostenoic acid |
| 52 | 4-trimethylsilyloxy-2-(6-carbotrimethylsilyloxy-2-cis-hexenyl)-cyclopent-2-en-1-one | 11α,16-dihydroxy-9-oxo-16-(1-propynyl)-20-ethyl-5-cis,13-trans-prostadienoic acid |
| 53 | 4-trimethylsilyloxy-2-(6-carbotrimethylsilyloxy-5-thiahexyl)-cyclopent-2-en-1-one | 11α,16-dihydroxy-9-oxo-16-(1-propynyl)-20-ethyl-3-thia-13-trans-prostenoic acid |
| 54 | 4-trimethylsilyloxy-2-(6-carbotrimethylsilyloxy-5-oxahexyl)-cyclopent-2-en-1-one | 11α,16-dihydroxy-9-oxo-16-(1-propynyl)-20-ethyl-3-oxa-13-trans-prostenoic acid |
| 55 | 2-(6-carbethoxyhexyl)-cyclopent-2-en-1-one | methyl-16-hydroxy-9-oxo-16-(1-propynyl)-20-ethyl-13-trans-prostenoate |
| 56 | 2-(6-carbomethoxy-2-cis-hexenyl)-cyclopent-2-en-1-one | ethyl-16-hydroxy-9-oxo-16-(1-propynyl)-20-ethyl-5-cis,13-trans-prostadienoate |
| 57 | 2-(6-carbethoxy-5-thiahexyl)-cyclopent-2-en-1-one | ethyl-16-hydroxy-9-oxo-16-(1-propynyl)-20-ethyl-3-thia-13-trans-prostenoate |
| 58 | 2-(6-carbethoxy-5-oxahexyl)-cyclopent-2-en-1-one | ethyl-16-hydroxy-9-oxo-16-(1-propynyl)-20-ethyl-3-oxa-13-trans-prostenoate |
| 59 | d-4-trimethylsilyloxy-2-(6-carbomethoxy-2-cis-hexenyl)-cyclopent-2-en-1-one | nat-methyl-11α,16-dihydroxy-9-oxo-16-(1-propynyl)-20-ethyl-5-cis,13-trans-prostadienoate |
| 60 | d-4-trimethylsilyloxy-2-(6-carbomethoxyhexyl)-cyclopent-2-en-1-one | nat-methyl-11α,16-dihydroxy-9-oxo-16-(1-propynyl)-20-ethyl-13-trans-prostenoate |

EXAMPLES 61–80

Treatment of the 9-oxo-11α,16-dihydroxy-16-trimethylsilylethynyl-prostanoids of Table 6 by the procedure of Example 6 is productive of the corresponding 9-oxo-11α,16-dihydroxy-16-ethynyl-prostanoid of the Table.

TABLE 6

| Example | Starting Prostanoid | Product Prostanoid |
|---|---|---|
| 61 | 21 | 11α, 16-dihydroxy-9-oxo-16-ethynyl-13-trans-prostenoic acid |
| 62 | 22 | 11α, 16-ethynyl-5-cis, 13-trans-prostadienoic acid |
| 63 | 23 | 11α, 16-dihydroxy-9-oxo-16-ethynyl-3-thia-13-trans-prostenoic acid |
| 64 | 24 | 11α, 16-dihydroxy-9-oxo-16-ethynyl-3-oxa-13-trans-prostenoic acid |
| 65 | 25 | methyl-16-hydroxy-9-oxo-16-ethynyl-5-cis, 13-trans-prostenoate |
| 66 | 26 | ethyl-16-hydroxy-9-oxo-16-ethynyl-5-cis, 13-trans-prostadienoate |
| 67 | 27 | ethyl-16-hydroxy-9-oxo-16-ethynyl-3-thia-13-trans-prostenoate |
| 68 | 28 | ethyl-16-hydroxy-9-oxo-16-ethynyl-3-oxa-13-trans-prostenoate |
| 69 | 29 | nat-methyl-11α, 16-dihydroxy-9-oxo-16-ethynyl-5-cis, 13-trans-prostadienoate |
| 70 | 30 | nat-methyl-11α, 16-dihydroxy-9-oxo-16-ethynyl-13-trans-prostenoate |
| 71 | 41 | 11α, 16-dihydroxy-9-oxo-16-ethynyl-20-ethyl-13-trans-prostenoic acid |
| 72 | 42 | 11α, 16-dihydroxy-9-oxo-16-ethynyl-20-ethyl-5-cis,-13-trans-prostadienoic acid |
| 73 | 43 | 11α, 16-dihydroxy-9-oxo-16-ethynyl-20-ethyl-3-thia-13-trans-prostenoic acid |
| 74 | 44 | 11α, 16-dihydroxy-9-oxo-16-ethynyl-20-ethyl-3-oxa-13-trans-prostenoic acid |
| 75 | 45 | methyl-16-hydroxy-9-oxo-16-ethynyl-20-ethyl-13-trans-prostenoate |
| 76 | 46 | ethyl-16-hydroxy-9-oxo-16-ethynyl-20-ethyl-5-cis,-13-trans-prostadienoate |
| 77 | 47 | ethyl-16-hydroxy-9-oxo-16-ethynyl-3-thia-13-trans-prostenoate |
| 78 | 48 | ethyl-16-hydroxy-9-oxo-16-ethynyl-20-ethyl-3-oxa-5-cis, 13-trans-prostenoate |
| 79 | 49 | nat-methyl-11α,16-dihydroxy-9-oxo-16-ethynyl-20-ethyl-5-cis, 13-trans-prostadienoate |
| 80 | 50 | nat-methyl-11α, 16-dihydroxy-9-oxo-16-ethynyl-20- |

TABLE 6-continued

| Example | Starting Prostanoid | Product Prostanoid |
|---------|---------------------|--------------------|
|         |                     | ethyl-13-trans-prostenoate |

EXAMPLES 81–96

Saponification of Examples 35–38, 65–68, 55–58, and 75–78 by the procedure described in Example is productive of the corresponding 9-oxo-16-hydroxy-16-ethynyl-prostenoic, 9-oxo-16-hydroxy-16-ethynyl-prostadienoic, 9-oxo-16-hydroxy-16-(1-propynyl)-prostenoic and 9-oxo-16-hydroxy-16-(1-propynyl)-prostadienoic acids.

EXAMPLES 97–120

Treatment of the prostanoic acids of Examples 21–24, 31–34, 41–44, 51–54, 61–64 and 71–74 with diazomethane in ether is productive of the corresponding methyl prostanoate.

EXAMPLES 121–144

Treatment of the prostanoic acid of Examples 21–24, 31–34, 41–44, 51–54, 61–64 and 71–74 with diazohexane is productive of the corresponding hexyl prostanoate.

EXAMPLES 145–149

Treatment of the carboxy-cyclopentenones or carbomethoxy-cyclopentenones of Table 7 with chlorotrimethylsilane by the procedure described in U.S. Pat. No. 3,873,607 (Example 958) is productive of the bis-trimethylsilylether esters or trimethylsilylether methyl esters of the Table.

concentrated to give a liquid, pmr spectrum (CDCl$_3$): δ 3.59 (triplet, C$\underline{H}_2$Cl) and 4.70 (triplet, CH$_2$C$\underline{H}$OH).

EXAMPLE 151

Preparation of 5-(Carbethoxymethylthio)-1-(2-furyl)-1-pentanol

To a stirred, refluxing mixture of 76 g of ethyl mercaptoacetate, 79.5 g (Example 150), and 10 ml of 1.5 M sodium ethoxide in ethanol is added an additional 300 ml of 1.5 M sodium ethoxide during 15 minutes. The resulting mixture is stirred at reflux for 3 hours, cooled, and concentrated to remove most of the ethanol. The residue is partitioned with ether and water. The ether phase is washed with brine and dried over potassium carbonate. The solution is concentrated, diluted with xylene, and again concentrated to give an oil, pmr spectrum (CDCl$_3$): δ 3.24 (singlet, -SC$\underline{H}_2$CH$_3$) and 4.70 (triplet, CH$_2$C$\underline{H}$OH).

EXAMPLE 152

Preparation of 4-Hydroxy-2-[4-(carboxymethylthio)butyl]-cyclopent-2-en-1-one

A stirred solution of 125 g of 5-(carbethoxymethylthio)-1-(2-furyl)-1-pentanol (Example 151), 22.4 g of sodium formate, 250 ml of formic acid, and 400 mg of hydroquinone in 2000 ml of dioxane and 1330 ml of

TABLE 7

| Example | Starting Cyclopentenone | Product Ether |
|---------|------------------------|---------------|
| 145 | 2-(6-carboxyhexyl)-4-hydroxycyclopent-2-en-1-one[1] | 4-trimethylsiloxy-2-(6-carbotrimethylsiloxyhexyl)-cyclopent-2-en-1-one |
| 146 | 1-2-(6-carbomethoxyhexyl)-4-hydroxycyclopent-2-en-1-one[2] | 1-4-trimethylsiloxy-2-(6-carbomethoxy)-cyclopent-2-en-1-one |
| 147 | 1-2-(6-carbomethoxy-2-cis-hexenyl)-4-hydroxycyclopent-2-en-1-one[3] | 1-4-trimethylsiloxy-2-(6-carbomethoxy-2-cis-hexenyl)cyclopent-2-en-1-one |
| 148 | 2-(6-carboxy-2-cisoctenyl)-4-hydroxycyclopent-2-en-1-one[4] | 2-(6-carbotrimethysiloxy-2-cis-octenyl)-4-trimethylsiloxycyclopent-2-en-1-one |
| 149 | 2-(6-carboxy-5-oxahexyl)-4-hydroxycyclopent-2-en-1-one[4] | 4-trimethylsiloxy-2-(6-carbotrimethsiloxy-5-oxahexyl)-cyclopent-2-en-1-one |

References:
[1] U.S. Pat. 3,873,607
[2] Pappo, et al., Tetrahedron Letters, 943 (1973)
[3] Bruhn, et [4] Ibid., 235 (1976)
4. U.S. Pat. 3,950,406

EXAMPLE 150

Preparation of 5-Chloro-1-(2-furyl)-1-pentanol

To a stirred suspension of 2-furyllithium [prepared from 0.53 moles of n-butyllithium and 39.5 g of furan by the procedure of J. Org. Chem., 27, 1216 (1962)] in 350 ml of ether and with 200 ml of hexane at −78° C. is added a solution of 57.9 g of 5-chloropentanol [Chem. Abstr., 59, 7579F (1963)] in 80 ml of ether during 25 minutes. The mixture is warmed to 0° C. during 20 minutes, stirred at 0° C. for 15 minutes, and treated with 140 ml of saturated ammonium chloride. The ether phase is washed with water and brine, dried over magnesium sulfate and potassium carbonate mixture, and water is refluxed for 20 hours.

The solution, containing crude 3-hydroxy-2-[4-(carbethoxymethylthio)butyl]cyclopent-4-en-1-one, is cooled and treated during 10 minutes with 75 ml of sulfuric acid (d=1.84) with stirring. The stirred solution is refluxed for 16 hours, cooled, saturated with sodium chloride, and extracted with ethyl acetate. The extract is washed with brine, dried over magnesium sulfate, and concentrated. The residue is subjected to chromatography on silica gel with chloroform progressively enriched in ether, ether, and ether progressively enriched in acetone to afford the subject compound as an oil; pmr spectrum (CDCl$_3$): δ 3.24 (singlet, —SC$\underline{H}_2$CH$_3$), 5.0

(broad singlet, —C$\underline{H}$OH—), and 7.38 (singlet, vinyl hydrogen).

EXAMPLE 153

Preparation of 2-[4-(Carbotrimethylsiloxymethylthio)-butyl]-4-trimethylsiloxycyclopent-2-en-1-one To a stirred solution of 28.4 g of 4-hydroxy-2-[4-(carboxymethylthio)butyl]cyclopent-2-en-1-one (Example 152) and 76 ml of hexamethyldisilazone in 330 ml of pyridine at 5° C. is added 38 ml of chlorotrimethylsilane during 5 minutes. The mixture is stirred at ambient temperature for 3.5 hours, at 45° C. for 5 minutes, and then evaporated to remove solvent. The residue is stirred with 1000 ml of petroleum ether and filtered. The filtrate is treated with charcoal and filtered; this filtrate is concentrated with the aid of toluene to give a liquid, pmr spectrum (CDCl$_3$): δ 0.18 (singlet, trimethylsiloxy group) and 0.28 (singlet, trimethylsiloxycarbonyl group).

EXAMPLE 154

Preparation of 9-Oxo-16-hydroxyl-6-ethynyl-5-cis,10,13-trans-prostatrienoic acid To a stirred solution of 9-oxo-11α,16-dihydroxy-16-ethynyl-5-cis,13-trans-prostadienoic acid (Example 62) in pyridine is added acetic anhydride. After standing for 5 hours at room temperature, the solution is stirred with a mixture of ethyl acetate and 1 M aqueous sodium bisulfate at 0° C. The ethyl acetate layer is washed with brine and concentrated in the presence of toluene.

The residue, consisting of crude 9-oxo-11α-acetoxy-16-hydroxy-16-vinyl-5-cis,13-trans-prostadienoic acid, is dissolved in methanol with potassium acetate. After standing for 18 hours at room temperature, the solution is partitioned with ethyl acetate and brine. The organic phase is washed with brine, dried over magnesium sulfate, and concentrated. The residue is purified by partition chromatography on Celite with the system heptane-dichloromethane-methanol-water (80:20:15:6) to give the product as an oil.

EXAMPLE 155

Treatment of the 9-oxo-11α,16-dihydroxy prostadienoic or prostenoic acids and esters of Examples 21-61, and 63-144 with acetic anhydride in pyridine followed by potassium acetate in methanol according to Example 68 furnishes the product 9-oxo-16-hydroxy-Δ$^{10}$-prostadienoic or prostatrienoic acids.

We claim:
1. An optically active compound of the formula:

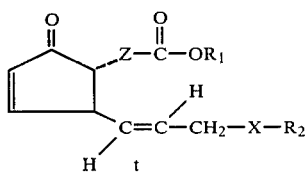

wherein R$_1$ is selected from the group consisting of hydrogen and C$_1$ to C$_6$ alkyl; R$_2$ is selected from the group consisting of C$_3$ to C$_7$ alkyl; X is selected from the group consisting of a divalent moiety of the formula:

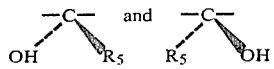

wherein R$_5$ is selected from the group consisting of ethynyl, 2-propynyl and trimethylsilylethynyl; Z is selected from the group consisting of —(CH$_2$)$_6$—, —(CH$_2$)$_4$SCH$_2$— and —(CH$_2$)$_4$—O—CH$_2$—; the racemic mixture thereof; and, when R$_1$ is hydrogen, the pharmacologically acceptable salts thereof.

2. A compound according to claim 1, wherein Z is —(CH$_2$)$_6$—.

3. A compound according to claim 2, wherein Z is selected from the group consisting of —(CH$_2$)$_4$OCH$_2$— and —(CH$_2$)$_4$—S—CH$_2$.

4. A compound according to claim 2, wherein R$_3$ is hydroxyl.

5. A compound according to claim 2, wherein R$_3$ is hydrogen.

6. A compound according to claim 3, wherein R$_3$ is hydroxyl.

7. A compound according to claim 3, wherein R$_3$ is hydrogen.

8. The optically active compound according to claim 4, nat. methyl-16-hydroxy-9-oxo-16-ethynyl-Δ$^{10}$,13-trans-prostadienoate.

9. The optically active compound according to claim 4, nat. 16-hydroxy-9-oxo-16-ethynyl-Δ$^{10}$,13-trans-prostadienoic acid.

10. The optically active compound according to claim 4, nat. methyl-16-hydroxy-9-oxo-16-ethynyl-Δ$^{10}$,13-trans-prostadienoate.

11. The optically active compound according to claim 4, nat. 16-hydroxy-9-oxo-16-ethynyl-20-ethyl-Δ$^{10}$,13-trans-prostadienoic acid.

12. The optically active compound according to claim 4, nat. methyl-16-hydroxy-9-oxo-16-(1-propynyl)-Δ$^{10}$,13-trans-prostadienoate.

13. The optically active compound according to claim 4, nat. 16-hydroxy-9-oxo-16-(1-propynyl)-Δ$^{10}$,13-trans-prostadienoic acid.

14. The optically active compound according to claim 4, nat. methyl-16-hydroxy-9-oxo-16-(1-propynyl)-20-ethyl-Δ$^{10}$,13-trans-prostadienoate.

15. The optically active compound according to claim 4, nat. 16-hydroxy-9-oxo-16-(1-propynyl)-20-ethyl-Δ$^{10}$,13-trans-prostadienoic acid.

16. The optically active compound according to claim 4, nat. methyl-16-hydroxy-9-oxo-16-trimethylsilylethynyl-Δ$^{10}$,13-trans-prostadienoate.

17. The optically active compound according to claim 4, nat. 16-hydroxy-9-oxo-16-trimethylsilylethynyl-Δ$^{10}$,13-trans-prostadienoic acid.

18. The optically active compound according to claim 4, nat. methyl-16-hydroxy-9-oxo-16-trimethylsilylethynyl)-20-ethyl-Δ$^{10}$,13-trans-prostadienoate.

19. The optically active compound according to claim 4, nat. 16-hydroxy-9-oxo-16-trimethylsilylethynyl-20-ethyl-Δ$^{10}$,13-trans-prostadienoic acid.

20. The racemic compound according to claim 4, dl-16-hydroxy-9-oxo-16-ethynyl-Δ$^{10}$,13-trans-prostadienoic acid.

21. The racemic compound according to claim 4, dl-hexyl-16-hydroxy-9-oxo-16-ethynyl-20-ethyl-Δ$^{10}$,13-trans-prostadienoate.

22. The optically active compound according to claim 4, nat. methyl-16-hydroxy-9-oxo-16-(1-propynyl)-$\Delta^{10,13}$-trans-prostadienoate.

23. The racemic compound according to claim 4, dl-16-hydroxy-9-oxo-16-(1-propynyl)-20-ethyl-$\Delta^{10,13}$-trans-prostadienoic acid.

24. The racemic compound according to claim 4, dl-16-hydroxy-9-oxo-16-trimethylsilylethynyl-$\Delta^{10,13}$-trans-prostadienoic acid.

25. The racemic compound according to claim 4, dl-methyl-16-hydroxy-9-oxo-16-trimethylsilylethynyl-20-ethyl-$\Delta^{10,13}$-trans-prostadienoate.

26. The optically active compound according to claim 4, nat. 16-hydroxy-9-oxo-16-trimethylsilylethynyl-20-ethyl-5,6-cis,$\Delta^{10,13}$-trans-prostatrienoic acid.

27. The racemic compound according to claim 5, dl-16-hydroxy-9-oxo-16-ethynyl-$\Delta^{10,13}$-trans-prostadienoic acid.

28. The racemic compound according to claim 5, dl-hexyl-16-hydroxy-9-oxo-16(propynyl)-$\Delta^{10,13}$-trans-prostadienoate.

29. The racemic compound according to claim 5, dl-16-hydroxy-9-oxo-16-trimethylsilylethynyl-$\Delta^{10,13}$-trans-prostadienoic acid.

30. The racemic compound according to claim 6, dl-methyl-16-hydroxy-9-oxo-16-ethynyl-3-thia-$\Delta^{10,13}$-trans-prostadienoate.

31. The racemic compound according to claim 6, dl-16-hydroxy-9-oxo-16-ethynyl-20-ethyl-3-thia-$\Delta^{10,13}$-trans-prostadienoic acid.

32. The racemic compound according to claim 6, dl-methyl-16-hydroxy-9-oxo-16-(1-propynyl)-3-thia-$\Delta^{10,13}$-trans-prostadienoate.

33. The racemic compound according to claim 6, dl-16-hydroxy-9-oxo-16-(1-propynyl)-20-ethyl-3-thia-$\Delta^{10,13}$-trans-prostadienoic acid.

34. The racemic compound according to claim 6, dl-hexyl-16-hydroxy-9-oxo-16-trimethylsilylethynyl-3-thia-$\Delta^{10,13}$-trans-prostadienoate.

35. The racemic compound according to claim 6, dl-16-hydroxy-9-oxo-16-trimethylsilylethynyl-20-ethyl-3-thia-$\Delta^{10,13}$-trans-prostadienoic acid.

36. The racemic compound according to claim 6, dl-16-hydroxy-9-oxo-16-ethynyl-3-oxa-$\Delta^{10,13}$-trans-prostadienoic acid.

37. The racemic compound according to claim 6, dl-hexyl-16-hydroxy-9-oxo-16-ethynyl-20-ethyl-3-oxa-$\Delta^{10,13}$-trans-prostadienoate.

38. The racemic compound according to claim 6, dl-16-hydroxy-9-oxo-16-(1-propynyl)-3-oxa-$\Delta^{10,13}$-trans-prostadienoic acid.

39. The racemic compound according to claim 6, dl-hexyl-16-hydroxy-9-oxo-16-(1-propynyl)-20-ethyl-3-oxa-$\Delta^{10,13}$-trans-prostadienoate.

40. The racemic compound according to claim 6, dl-16-hydroxy-9-oxo-16-trimethylsilylethynyl-3-oxa-$\Delta^{10,13}$-trans-prostadienoic acid.

41. The racemic compound according to claim 6, dl-methyl-16-hydroxy-9-oxo-16-trimethylsilylethynyl-20-ethyl-3-oxa-$\Delta^{10,13}$-trans-prostadienoate.

42. The racemic compound according to claim 7, dl-16-hydroxy-9-oxo-16-ethynyl-3-thia-$\Delta^{10,13}$-trans-prostadienoic acid.

43. The racemic compound according to claim 6, dl-methyl-16-hydroxy-9-oxo-16-ethynyl-20-ethyl-3-oxa-$\Delta^{10,13}$-trans-prostadienoate.

44. The racemic compound according to claim 7, dl-hexyl-16-hydroxy-9-oxo-16-(1-propynyl)-3-thia-$\Delta^{10,13}$-trans-prostadienoate.

45. The racemic compound according to claim 7, dl-16-hydroxy-9-oxo-16-(1-propynyl)-20-ethyl-3-oxa-$\Delta^{10,13}$-trans-prostadienoic acid.

46. The racemic compound according to claim 7, dl-methyl-16-hydroxy-9-oxo-16-triemthylsilylethynyl-3-thia-$\Delta^{10,13}$-trans-prostadienoate.

47. The racemic compound according to claim 7, dl-16-hydroxy-9-oxo-16-trimethylsilylethynyl-20-ethyl-3-oxa-$\Delta^{10,13}$-trans-prostadienoic acid.

* * * * *